United States Patent
Rubnov et al.

(10) Patent No.: US 12,251,380 B2
(45) Date of Patent: *Mar. 18, 2025

(54) DEPOT SYSTEMS COMPRISING CARIPRAZINE OR SALTS THEREOF

(71) Applicant: Mapi Pharma Ltd., Ness Ziona (IL)

(72) Inventors: Shai Rubnov, Tel Aviv (IL); Ehud Marom, Tel Aviv (IL); Anna Gopin, Petah-Tiqwa (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,682

(22) Filed: Feb. 8, 2024

(65) Prior Publication Data
US 2024/0238280 A1  Jul. 18, 2024

Related U.S. Application Data

(63) Continuation of application No. 18/109,328, filed on Feb. 14, 2023, now Pat. No. 11,931,357.
(Continued)

(51) Int. Cl.
*A61K 31/496* (2006.01)
*A61K 9/08* (2006.01)
*A61K 47/69* (2017.01)

(52) U.S. Cl.
CPC .............. *A61K 31/496* (2013.01); *A61K 9/08* (2013.01); *A61K 47/6937* (2017.08)

(58) Field of Classification Search
None
See application file for complete search history.

(56) References Cited

U.S. PATENT DOCUMENTS 11,931,357 B2 * 3/2024 Rubnov ................. A61K 47/34
2008/0063687 A1   3/2008 Chou
(Continued)

FOREIGN PATENT DOCUMENTS

CN       108261394 A    7/2018
WO    2018015915 A1    1/2018
(Continued)

OTHER PUBLICATIONS

Kanwar and Sinha (2019) In Situ Forming Depot as Sustained-Release Drug Delivery Systems. Crit Rev Ther Drug Carrier Syst 36(2): 93-136.

*Primary Examiner* — Dominic Lazaro
(74) *Attorney, Agent, or Firm* — ROTHWELL, FIGG, ERNST & MANBECK, P.C.

(57) ABSTRACT

The present invention provides long-acting parenteral pharmaceutical compositions including a therapeutically effective amount of Cariprazine or salts thereof, in a depot form suitable for administering at a medically acceptable location in a subject in need thereof. The depot compositions are preferably in the form of in-situ implants suitable for subcutaneous or intramuscular administration and provide prolonged release of the Cariprazine active ingredient and/or its metabolites desmethyl Cariprazine (DCAR) and didesmethyl Cariprazine (DDCAR) for a period of at least 4 weeks following a single administration. The present invention further provides methods of use of the depot compositions for the treatment of schizophrenia, major depressive disorder, and bipolar disorder.

20 Claims, 4 Drawing Sheets

Related U.S. Application Data

(60) Provisional application No. 63/320,706, filed on Mar. 17, 2022.

(56) References Cited

U.S. PATENT DOCUMENTS

| | | |
|---|---|---|
| 2011/0015208 A1 | 1/2011 | Samoriski |
| 2012/0046302 A1 | 2/2012 | Papadakis |
| 2021/0177768 A1 | 6/2021 | Hui |
| 2021/0283209 A1 | 9/2021 | Marom |

FOREIGN PATENT DOCUMENTS

| | | |
|---|---|---|
| WO | 2018229641 A1 | 12/2018 |
| WO | 2022003662 A1 | 1/2022 |

\* cited by examiner

DEPOT SYSTEMS COMPRISING CARIPRAZINE OR SALTS THEREOF

CROSS-REFERENCE TO RELATED APPLICATIONS

This application is a continuation of U.S. patent application Ser. No. 18/109,328 filed on Feb. 14, 2023, which claims the benefit of U.S. Provisional Application No. 63/320,706, filed on Mar. 17, 2022. The entirety of the disclosure of the above-referenced application is incorporated herein by reference.

FIELD OF THE INVENTION

The present invention relates to parenteral long-acting dosage forms of Cariprazine or its pharmacologically active salts, e.g., depot systems which provide prolonged release of Cariprazine and are intended for the treatment of schizophrenia, major depressive disorder, and bipolar disorder.

BACKGROUND OF THE INVENTION

Cariprazine HCl (VRAYLAR®), is an atypical antipsychotic. Cariprazine HCl is chemically named trans-N-{4-[2-[4-(2,3-dichlorophenyl)piperazine-1-yl]ethyl]cyclohexyl}-N',N'-dimethylurea hydrochloride, and its chemical structure is represented by the following formula:

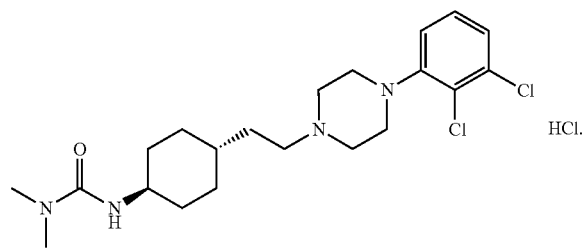 [SMILES: CN(C)C(=O)N[C@H]1CC[C@H](CCN2CCN(c3cccc(Cl)c3Cl)CC2)CC1]

Cariprazine is indicated for (1) the treatment of schizophrenia in adults; (2) acute treatment of manic or mixed episodes associated with bipolar I disorder in adults; and (3) treatment of depressive episodes associated with bipolar I disorder (bipolar depression) in adults. The mechanism of action of Cariprazine in treating schizophrenia and bipolar I disorder is unknown. However, it is thought that the efficacy of Cariprazine could be mediated through a combination of partial agonist activity at central dopamine D2 and serotonin 5-HT1A receptors and antagonist activity at serotonin 5-HT2A receptors. Cariprazine forms two major metabolites, desmethyl Cariprazine (DCAR) and didesmethyl Cariprazine (DDCAR) that have in vitro receptor binding profiles similar to the parent drug.

Cariprazine is orally administered in once-daily capsules with or without food. Like most lipophilic antipsychotics, it undergoes extensive hepatic metabolism by Cytochrome P450 (CYP), mainly 3A4, with the formation of active metabolites. However, the compound—particularly its active didesmethyl metabolite—is cleared very slowly, with elimination half-lives in schizophrenic patients ranging from 2-5 days for Cariprazine to 2-3 weeks for didesmethyl Cariprazine.

Oral administration of Cariprazine is known to be associated with severe and potentially fatal side effects including, in particular, increased risk of death in elderly people with dementia related psychosis, increased risk of suicidal thoughts or actions in children and young adults, stroke, neuropleptic malignant syndrome (NMS), tardive dyskinesia, metabolic problems such as high blood sugar and diabetes, low white blood cell count, decreased blood pressure, falls, seizures and difficulties in controlling body temperature.

Slow-release compositions giving rise to lower exposure of Cariprazine and its metabolites and a reduced side effect profile are desirable. However, no long-acting dosage forms of Cariprazine are available on the market.

PCT International Patent Publication No. WO 2018/015915 discloses a parenteral controlled release composition comprising an atypical antipsychotic, especially Lurasidone, and one or more rate controlling polymers, in the form of an in-situ gelling composition which forms a depot upon administration in vivo upon contact with body fluids thereby providing a prolonged release of the active agent.

Chinese Patent Application No. CN 108261394 discloses a Cariprazine hydrochloride injection preparation in the form of an aqueous suspension comprising a stabilizer, a suspending agent, a buffer, and a pH regulator. The particle size distribution and the injection dosage are controlled to achieve the long-acting effect, the Cariprazine hydrochloride is continuously released at least one week after the preparation is injected.

PCT International Patent Publication No. WO 2018/229641 discloses oral pharmaceutical compositions and methods for the modified release delivery of Cariprazine for less than daily dosing.

US Patent Application Publication No. US 2021/0177768 discloses a pharmaceutical composition comprising a therapeutically effective amount of an active agent selected from Cariprazine, a salt thereof, or a derivative thereof including a derivative salt form thereof, a biodegradable and biocompatible polymer comprising a polymeric matrix material, and a non-ionic water soluble colloid, wherein the active agent is ionically complexed with the biodegradable and biocompatible polymer or the active agent is dispersed in the matrix material, and wherein the composition is in the form of a microparticle, a microsphere, a nanoparticle, or a combination thereof.

There is an unmet need for long-acting dosage forms of Cariprazine, particularly for patients suffering from side effects of oral Cariprazine.

SUMMARY OF THE INVENTION

The present invention provides long-acting parenteral pharmaceutical compositions comprising a therapeutically effective amount of Cariprazine or its pharmaceutically acceptable salt, in particular Cariprazine HCl. In some embodiments, the present invention provides a long-acting pharmaceutical composition comprising a therapeutically effective amount of Cariprazine or a pharmaceutically acceptable salt thereof in a depot form, suitable for parenteral administration at a medically acceptable location in a subject in need thereof. The present invention further provides methods of treating schizophrenia, major depressive disorder, and bipolar disorder, especially manic or mixed episodes associated with bipolar I disorder, or depressive episodes associated with bipolar I disorder (bipolar depression), by parenterally administering a composition comprising a therapeutically effective amount of Cariprazine or salts thereof to a subject in need thereof.

The present invention is based in part on the unexpected finding that long acting Cariprazine formulations such as in-situ implants provide metronomic treatment with continuous flow of low dose of Cariprazine over an extended period of time, thus providing a dramatic improvement in the side effect profile. Surprisingly, it has now been discovered that the long-acting pharmaceutical compositions according to the principles of the present invention provide superior therapeutic efficacy as compared with conventional oral immediate release Cariprazine formulations, with reduced incidence and/or with reduced severity of side effects at the systemic level.

According to a first aspect, the present invention provides a long-acting parenteral pharmaceutical composition suitable for forming an in situ implant in a subject in need thereof following administration, the composition comprises a therapeutically effective amount of Cariprazine or a pharmaceutically acceptable salt thereof, a pharmaceutically acceptable biodegradable carrier comprising poly(lactic-co-glycolic acid) (PLGA) containing a molar ratio of lactic to glycolic monomers of from 50:50 to 85:15 and having an inherent viscosity in the range of about 0.1 to about 0.8 dl/g, and a biocompatible solvent, wherein the composition releases the Cariprazine or a pharmaceutically acceptable salt thereof for at least 4 weeks following a single administration.

According to one embodiment, the pharmaceutical composition is in the form of a solution. According to another embodiment, the pharmaceutical composition is in the form of a suspension.

According to some embodiments, the pharmaceutical composition comprises Cariprazine hydrochloride (Cariprazine HCl) as an active ingredient. According to other embodiments, the long-acting composition comprises a dose of from about 1 to about 500 mg of Cariprazine or a salt thereof (e.g., Cariprazine HCl) per injection, including each value within the specified range. According to other embodiments, the long-acting composition comprises a dose of from about 1 to about 100 mg of Cariprazine or a salt thereof (e.g., Cariprazine HCl) per injection, including each value within the specified range. According to yet other embodiments, the long-acting composition releases a daily dose of from about 1 to about 10 mg of Cariprazine or a salt thereof (e.g., Cariprazine HCl), including each value within the specified range.

According to some embodiments, the long-acting composition comprises from about 0.5% to about 20% of Cariprazine or a salt thereof (e.g., Cariprazine HCl) per injection, including each value within the specified range. According to other embodiments, the long-acting composition comprises from about 1% to about 10% of Cariprazine or a salt thereof (e.g., Cariprazine HCl) per injection, including each value within the specified range. According to yet other embodiments, the long-acting composition comprises from about 1% to about 5% of Cariprazine or a salt thereof (e.g., Cariprazine HCl) per injection, including each value within the specified range.

According to some embodiments, the long-acting composition comprises from about 10 to about 80 mg/mL of Cariprazine or a salt thereof (e.g., Cariprazine HCl) per injection, including each value within the specified range. According to other embodiments, the long-acting composition comprises from about 20 to about 60 mg/mL of Cariprazine or a salt thereof (e.g., Cariprazine HCl) per injection, including each value within the specified range. According to yet other embodiments, the long-acting composition comprises from about 20 to about 50 mg/mL of Cariprazine or a salt thereof (e.g., Cariprazine HCl) per injection, including each value within the specified range.

According to some embodiments, the composition is administered at a frequency of about once monthly to about once every 3 months, or any period in between.

According to other embodiments, the composition provides extended release of the Cariprazine active ingredient over a period of at least about one month to about three months, or any period in between.

According to certain embodiments, the composition is administered by an intramuscular injection.

According to some embodiments, the carrier is poly(lactic-co-glycolic acid) (PLGA) comprising lactic acid and glycolic acid end groups. According to some embodiments, the carrier is poly(lactic-co-glycolic acid) (PLGA) comprising lactic acid ester and glycolic acid ester end groups.

According to some embodiments, the poly(lactic-co-glycolic acid) (PLGA) contains a molar ratio of lactic to glycolic monomers of 50:50. According to some embodiments, the poly(lactic-co-glycolic acid) (PLGA) contains a molar ratio of lactic to glycolic monomers of 75:25. According to some embodiments, the poly(lactic-co-glycolic acid) (PLGA) contains a molar ratio of lactic to glycolic monomers of 85:15.

According to some embodiments, the poly(lactic-co-glycolic acid) (PLGA) has an inherent viscosity in the range of about 0.2 to about 0.7 dl/g, including each value within the specified range. According to some embodiments, the poly(lactic-co-glycolic acid) (PLGA) has an inherent viscosity in the range of about 0.3 to about 0.7 dl/g, including each value within the specified range. According to some embodiments, the poly(lactic-co-glycolic acid) (PLGA) has an inherent viscosity in the range of about 0.4 to about 0.6 dl/g, including each value within the specified range.

According to some embodiments, the composition comprises a single PLGA polymer. According to other embodiments, the composition comprises a combination of two or more PLGA polymers having different inherent viscosities. According to yet other embodiments, the composition comprises a combination of two PLGA polymers having different inherent viscosities. According to further embodiments, the ratio between the PLGA polymer having a higher inherent viscosity and the PLGA polymer having a lower inherent viscosity ranges from 2:1 to 1:1. According to additional embodiments, the combination of PLGA polymers has an inherent viscosity in the range of about 0.4 to about 0.6 dl/g, including each value within the specified range.

According to some embodiments, the ratio between the Cariprazine or a pharmaceutically acceptable salt thereof and the PLGA polymer is about 1:1 to about 1:100, preferably about 1:5 to about 1:25, including each value within the specified ranges.

According to some embodiments, the biocompatible solvent is selected from the group consisting of benzyl alcohol, methyl benzoate, ethyl benzoate, n-propylbenzoate, isopropyl benzoate, butyl benzoate, isobutyl benzoate, tert-butyl benzoate, and benzyl benzoate. Each possibility represents a separate embodiment. According to one embodiment, the biocompatible solvent is benzyl alcohol.

According to further embodiments, the composition of the present invention further comprises one or more pharmaceutically acceptable excipients selected from the group consisting of preservatives, sustained release agents, buffering agents, pH adjusting agents, and any combination thereof. Each possibility represents a separate embodiment. According to one embodiment, the sustained release agent is a bile salt selected from the group consisting of sodium glycocholate, sodium deoxycholate, sodium taurocholate, sodium fusidate, sodium glycodeoxycholate, and sodium taurodihydrofusidate. Each possibility represents a separate embodiment. According to another embodiment, the sustained release agent is selected from the group consisting of triethyl citrate, triacetin, and lecithin. Each possibility represents a separate embodiment. According to yet another embodiment, the pH adjusting agent comprises a carboxylic acid selected from the group consisting of benzoic acid, sorbic acid, fumaric acid, adipic acid, citric acid, succinic acid, glutaric acid, malic acid, malonic acid, tartaric acid, acetic acid, glycolic acid, propionic acid, lauric acid, caprylic acid, capric acid, and myristic acid. Each possibility represents a separate embodiment.

According to some embodiments, the composition provides less than about 20% burst release of the Cariprazine or pharmaceutically acceptable salt thereof in an aqueous medium containing 0.1% sodium lauryl sulfate as measured using a dissolution apparatus type II. According to some embodiments, the composition provides from about 2% to about 19% burst release of the Cariprazine or pharmaceutically acceptable salt thereof in an aqueous medium containing 0.1% sodium lauryl sulfate as measured using a dissolution apparatus type II.

According to some embodiments, the composition releases less than 40% of the Cariprazine or pharmaceutically acceptable salt thereof within 1 week in an aqueous medium containing 0.1% sodium lauryl sulfate as measured using a dissolution apparatus type II. According to some embodiments, the composition releases less than 30% of the Cariprazine or pharmaceutically acceptable salt thereof within 1 week in an aqueous medium containing 0.1% sodium lauryl sulfate as measured using a dissolution apparatus type II. According to some embodiments, the composition releases less than 20% of the Cariprazine or pharmaceutically acceptable salt thereof within 1 week in an aqueous medium containing 0.1% sodium lauryl sulfate as measured using a dissolution apparatus type II. According to some embodiments, the composition releases from about 8% to about 40% of the Cariprazine or pharmaceutically acceptable salt thereof within 1 week in an aqueous medium containing 0.1% sodium lauryl sulfate as measured using a dissolution apparatus type II.

According to some embodiments, the composition releases less than 55% of the Cariprazine or pharmaceutically acceptable salt thereof within 2 weeks in an aqueous medium containing 0.1% sodium lauryl sulfate as measured using a dissolution apparatus type II. According to some embodiments, the composition releases less than 45% of the Cariprazine or pharmaceutically acceptable salt thereof within 2 weeks in an aqueous medium containing 0.1% sodium lauryl sulfate as measured using a dissolution apparatus type II. According to some embodiments, the composition releases less than 35% of the Cariprazine or pharmaceutically acceptable salt thereof within 2 weeks in an aqueous medium containing 0.1% sodium lauryl sulfate as measured using a dissolution apparatus type II. According to some embodiments, the composition releases from about 15% to about 53% of the Cariprazine or pharmaceutically acceptable salt thereof within 2 weeks in an aqueous medium containing 0.1% sodium lauryl sulfate as measured using a dissolution apparatus type II.

According to some embodiments, the composition releases less than 80% of the Cariprazine or pharmaceutically acceptable salt thereof within 3 weeks in an aqueous medium containing 0.1% sodium lauryl sulfate as measured using a dissolution apparatus type II. According to some embodiments, the composition releases less than 70% of the Cariprazine or pharmaceutically acceptable salt thereof within 3 weeks in an aqueous medium containing 0.1% sodium lauryl sulfate as measured using a dissolution apparatus type II. According to some embodiments, the composition releases less than 60% of the Cariprazine or pharmaceutically acceptable salt thereof within 3 weeks in an aqueous medium containing 0.1% sodium lauryl sulfate as measured using a dissolution apparatus type II. According to some embodiments, the composition releases from about 36% to about 71% of the Cariprazine or pharmaceutically acceptable salt thereof within 3 weeks in an aqueous medium containing 0.1% sodium lauryl sulfate as measured using a dissolution apparatus type II.

According to some embodiments, the composition releases less than 90% of the Cariprazine or pharmaceutically acceptable salt thereof within 4 weeks in an aqueous medium containing 0.1% sodium lauryl sulfate as measured using a dissolution apparatus type II. According to some embodiments, the composition releases less than 80% of the Cariprazine or pharmaceutically acceptable salt thereof within 4 weeks in an aqueous medium containing 0.1% sodium lauryl sulfate as measured using a dissolution apparatus type II. According to some embodiments, the composition releases less than 70% of the Cariprazine or pharmaceutically acceptable salt thereof within 4 weeks in an aqueous medium containing 0.1% sodium lauryl sulfate as measured using a dissolution apparatus type II. According to some embodiments, the composition releases from about 45% to about 86% of the Cariprazine or pharmaceutically acceptable salt thereof within 4 weeks in an aqueous medium containing 0.1% sodium lauryl sulfate as measured using a dissolution apparatus type II.

According to some embodiments, the composition releases more than 50% of the Cariprazine or pharmaceutically acceptable salt thereof within 5 weeks in an aqueous medium containing 0.1% sodium lauryl sulfate as measured using a dissolution apparatus type II. According to some embodiments, the composition releases more than 60% of the Cariprazine or pharmaceutically acceptable salt thereof within 5 weeks in an aqueous medium containing 0.1% sodium lauryl sulfate as measured using a dissolution apparatus type II. According to some embodiments, the composition releases more than 70% of the Cariprazine or pharmaceutically acceptable salt thereof within 5 weeks in an aqueous medium containing 0.1% sodium lauryl sulfate as measured using a dissolution apparatus type II. According to some embodiments, the composition releases from about 62% to about 92% of the Cariprazine or pharmaceutically acceptable salt thereof within 5 weeks in an aqueous medium containing 0.1% sodium lauryl sulfate as measured using a dissolution apparatus type II.

According to some embodiments, the composition provides therapeutically effective plasma concentrations of Cariprazine for at least 4 weeks following a single administration. According to some embodiments, the composition provides substantially constant Cariprazine plasma concentrations between about 60 hours to about 600 hours after a single administration, including each value within the specified range.

The present invention encompasses the use of the long acting Cariprazine composition disclosed herein in a method of treating schizophrenia, major depressive disorder, and/or bipolar disorder, especially manic or mixed episodes associated with bipolar I disorder and/or depressive episodes associated with bipolar I disorder (bipolar depression).

Thus, according to some embodiments, the present invention provides a method of treating a disease or disorder selected from schizophrenia, major depressive disorder, and bipolar disorder in a subject in need thereof, the method comprising administering to the subject the long-acting parenteral pharmaceutical composition disclosed herein. According to some embodiments, the present invention provides a long-acting parenteral pharmaceutical composition as disclosed herein for use in treating a disease or disorder selected from schizophrenia, major depressive disorder, and bipolar disorder. Each possibility represents a separate embodiment.

As contemplated herein, the depot compositions of the present invention provide equal or superior therapeutic efficacy as compared to a conventional immediate release oral Cariprazine formulation, with reduced incidence and/or with reduced severity of side effects at the systemic level. According to some embodiments, the compositions of the present invention provide prolonged release or prolonged action of Cariprazine and/or its metabolites desmethyl Cariprazine (DCAR) and didesmethyl Cariprazine (DDCAR) in a subject as compared to an immediate release oral formulation.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
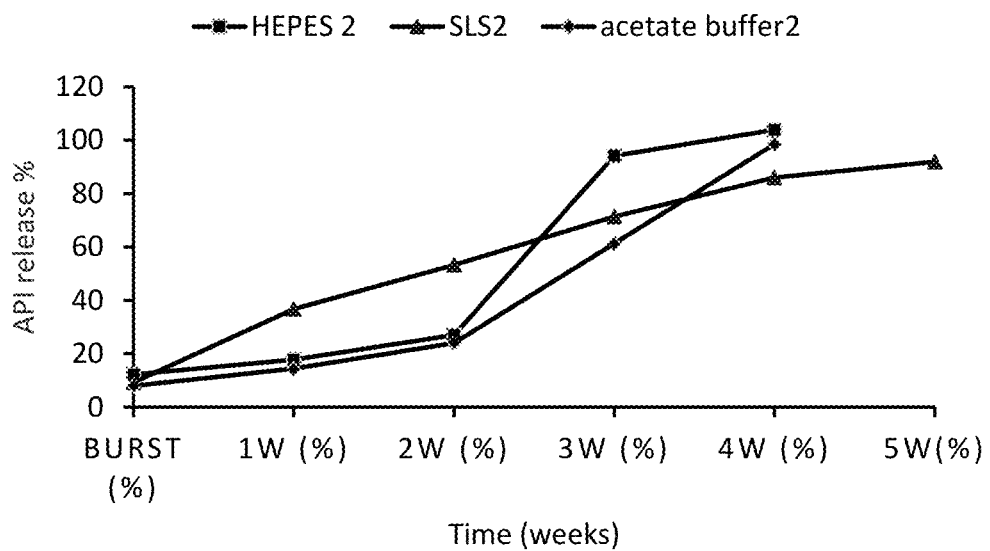
FIG. 1 shows Cariprazine release from Formulation A in 0.1% SLS, 0.1M HEPES, and 0.1M acetate buffer media.

The present invention provides long-acting in situ forming depot compositions of Cariprazine or salts thereof, in particular Cariprazine HCl, which afford superior therapeutic efficacy to the daily oral administrations and thus result in improved patient compliance. In addition to providing the superior therapeutic efficacy, the long-acting compositions reduce the Cariprazine side effects resulting from peak concentrations of the drug in the blood.

The present invention thus provides a long-acting parenteral pharmaceutical composition comprising a therapeutically effective amount of Cariprazine, or a pharmaceutically acceptable salt thereof, wherein the composition is in depot form suitable for administration at a medically acceptable location in a subject in need thereof. The depot composition may be adapted for subcutaneous or intramuscular administration.

Depot Systems

Oral administration of small molecules is the most common and effective form of delivery. However, the maximal duration of a drug product within the gastro-intestinal track is limited to 18-36 hours. This necessitates frequent drug dosing, which may reduce patient compliance. Reducing the frequency of oral drug administrations may be achieved through the use of long-acting pharmaceutical formulations such as injectable depot formulations that are capable of releasing the drug in a slow but predictable manner and consequently improve compliance. For most drugs, depending on the dose, it may be possible to reduce the administration frequency from daily administrations to once weekly, once or twice monthly or even longer (once every 3 to 6 months). In addition to improving patient compliance, less frequent administrations of drugs in the form of depot formulations smooths out the plasma concentration-time profile by eliminating the hills and valleys. Such smoothing out of plasma profiles has the potential to not only boost the therapeutic benefit, but also to reduce any undesired effects, such as those associated with Cariprazine oral administration.

Microparticles, implants and gels are the most common forms of biodegradable polymeric systems used in practice for prolonging the release of drugs in the body. Microparticles are typically suspended in aqueous media before injection to provide suspensions containing up to 40% solids. Implant/rod formulations may be delivered subcutaneously (SC) and/or intramuscularly (IM) with the aid of special needles in the dry state without the need for aqueous media.

While microparticle-based depot formulations as well as implant/rod formulations allow for higher doses of the active ingredient to be delivered, they often suffer from several disadvantages. The process for the preparation of microparticles typically involves a multi-step procedure that limits its application in drug delivery systems. Complex manufacturing procedures also pose difficulties in scaling up. Furthermore, parenteral sustained release suspensions are dispersed heterogeneous systems containing insoluble drug particles that need to be resuspended before administration. However, stability issues stemming from sedimentation of microparticles are often encountered thereby limiting the use of parenteral suspensions as drug delivery systems. While surgical implants show well controlled release profiles and reproducible manufacturing procedures, they require the surgical insertion of the implant inside the body which is often painful thereby resulting in poor patient compliance.

An alternative drug delivery system, i.e., an in situ forming biodegradable implant for extended release of the active ingredient constitutes a promising approach to overcome the problems of parenteral sustained release drug delivery systems in the form of microparticles or solid implants/rods. These systems are composed of biodegradable polymers dissolved in a biocompatible solvent. Otherwise in solution form, these systems transform into a gel after administration when in contact with bodily fluids. Drugs present in these systems become entrapped within the polymer matrix formed after gelation thereby affording their slow release by diffusion and upon degradation of the hardened gel matrix. These systems exhibit several advantages over other controlled release systems. In situ forming systems are prepared in a single-step process, which reduces process variabilities and results in product uniformity and reproducibility. Additional advantages include biocompatibility with biological systems, solubilization of low-molecular-weight hydrophobic drugs, and controlled release for weeks to months (Critical Reviews™ in Therapeutic Drug Carrier Systems, 36(2):93-136 (2019)).

According to the principles of the present invention, the composition disclosed herein is administered parenterally. The term "parenteral" as used herein refers to routes of administration selected from subcutaneous (SC), intravenous (IV), intramuscular (IM), intradermal (ID), intraperitoneal (IP), and the like. Each possibility represents a separate embodiment. According to particular embodiments, the composition is administered via the intramuscular (IM) route.

According to the principles of the present invention, the composition which is in the form of a solution or suspension, is configured to form an in-situ implant in a subject following administration thereby forming an in-situ depot system that is long-acting. The term "long-acting" as used herein refers to a composition which provides prolonged, sustained, or extended release of the Cariprazine active ingredient to the general systemic circulation of a subject or to local sites of action in a subject. This term may further refer to a composition which provides prolonged, sustained or extended duration of action of the Cariprazine and/or its metabolites desmethyl Cariprazine (DCAR) and didesmethyl Cariprazine (DDCAR) in a subject.

Depending on the desired duration of action required, each depot formulation typically contains between about 1 and about 500 mg of the active ingredient, including each value within the specified range. Alternative suitable doses include, but are not limited to, about 1 mg to about 100 mg, about 5 mg to about 100 mg, about 1 mg to about 50 mg, about 10 mg to about 50 mg, about 20 mg to about 500 mg, and the like, including each value within the specified ranges. However, it is understood that the amount of the Cariprazine administered will be determined by a physician, according to various parameters including, the route of administration, the age, weight, and the severity of the patient's symptoms.

According to various embodiments of the present invention, the therapeutically effective amount of the Cariprazine ranges from about 1 mg to about 10 mg/day, including each value within the specified range, for an average adult weighing about 70 kg. Alternatively, such therapeutically effective amount of Cariprazine ranges from about 1.5 mg to about 6 mg/day, including each value within the specified range. Alternatively, such therapeutically effective amount of Cariprazine ranges from about 3 mg to about 6 mg/day, including each value within the specified range.

In some embodiments, the concentration of the Cariprazine in the formulations of the invention ranges from about 10 mg/mL to about 80 mg/mL, including each value within the specified range. In other embodiments, the concentration of the Cariprazine in the formulations of the invention ranges from about 20 mg/mL to about 60 mg/mL, including each value within the specified range. In other embodiments, the concentration of the Cariprazine in the formulations of the invention ranges from about 20 mg/mL to about 50 mg/mL, including each value within the specified range. In other embodiments, the concentration of the Cariprazine in the formulations of the invention ranges from about 10 mg/mL to about 100 mg/mL, including each value within the specified range.

In some embodiments, the concentration of the Cariprazine in the formulations of the invention is about 0.5% to about 20%, including each value within the specified range. In other embodiments, the concentration of the Cariprazine in the formulations of the invention is about 1% to about 10%, including each value within the specified range. In yet other embodiments, the concentration of the Cariprazine in the formulations of the invention is about 1% to about 5%, including each value within the specified range.

As contemplated herein, the depot compositions of the present invention are designed to be administered once in every period of about 4 weeks to about 6 months, and to provide prolonged release of the Cariprazine active ingredient over this timeframe. The depot compositions can be adapted to release the Cariprazine active ingredient over a desired period of time, for example over a period of about one month, or over a period of about 3 months or any period in between. Thus, by way of illustration and not by limitation, the composition of the present invention can be conveniently injected at a frequency of once every 4 weeks, once a month, once every 2 months, once every 3 months, once every 4 months, once every 5 months, once every 6 months, or any period therebetween. Each possibility represents a separate embodiment of the present invention.

The term "Cariprazine" as used herein refers to the compound trans-N-{4-[2-[4-(2,3-dichlorophenyl)piperazine-1-yl]ethyl]cyclohexyl}-N',N'-dimethylurea. The present invention also includes salts of Cariprazine. The term "salt" as used herein encompasses both basic and acid addition salts including, but not limited to, acid addition salts of amine nitrogens with organic or inorganic acids. Such acids include, but are not limited to, hydrochloric, hydrobromic, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like. Each possibility represents a separate embodiment of the present invention. A currently preferred Cariprazine salt is Cariprazine hydrochloride (Cariprazine HCl).

The present invention also includes solvates of Cariprazine and salts thereof. The term "solvate" as used herein refers to a physical association of Cariprazine or its salt with one or more solvent molecules. This physical association involves varying degrees of ionic and covalent bonding, including hydrogen bonding. In certain instances, the solvate may be isolated. "Solvate" encompasses both solution-phase and isolatable solvates. Non-limiting examples of suitable solvates include ethanolates, methanolates and the like. Each possibility represents a separate embodiment. When the solvent is water, the Cariprazine is a hydrate. The term "hydrate" encompasses, but is not limited to monohydrate, dihydrate, trihydrate, tetrahydrate, pentahydrate, hemihydrate, sesquihydrate, hemipentahydrate, and the like. Each possibility represents a separate embodiment.

The present invention also includes polymorphs of Cariprazine or Cariprazine salts. "Polymorph" as used herein refers to a particular crystalline state of a substance, which can be characterized by particular physical properties such as X-ray diffraction, IR spectra, Raman spectra, melting point, and the like.

In some embodiments, the depot formulations of the present invention are in the form of solutions or suspensions of Cariprazine or a pharmaceutically acceptable salt thereof in water, oil or wax phase, poorly soluble polyelectrolyte complexes of Cariprazine or its pharmaceutically acceptable salt thereof, and "in-situ" gel-forming matrices based on the combination of water-miscible solvent with Cariprazine or a pharmaceutically acceptable salt thereof. Each possibility represents a separate embodiment of the invention. According to certain embodiments, the depot formulations of the present invention do not contain microparticles, microspheres, nanoparticles or nanospheres.

In certain embodiments, the dosage forms include, but are not limited to, biodegradable injectable compositions, also known as injectable ISI (in situ implants), that are solutions or suspensions capable of forming depot systems upon administration when in contact with bodily fluids. The formation of the depot system is afforded by the presence of a biodegradable polymer and a water miscible solvent. Once the composition contacts the bodily fluids, the polymer gels or hardens forming a solid or a semisolid implant that entraps the active ingredient within a polymer matrix. Upon biodegradation of the polymer matrix, the active ingredient is released in a continuous and sustained manner.

The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly(D,L-lactide) i.e. PLA; glycolic acid-based polymers such as polyglycolides (PGA) e.g. Lactel® from Durect; poly(D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as poly(ε-caprolactone) i.e. PCL (Lactel® from Durect); polyanhydrides; poly(sebacic acid) SA; poly(ricinoleic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy}propane), CPP; poly(p-{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly(N-isopropylacrylamide) (PNIPAAm), poly(ethylene oxide)-poly(propylene oxide)-poly(ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof. Each possibility represents a separate embodiment.

According to the principles of the present invention, the biodegradable polymers include, but are not limited to, polylactides, polyglycolides, polycaprolactones, polyanhydrides, gelatin, collagen, celluloses, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxy valerates, polyalkylene oxalates, polyalkylene succinates, poly(malic acid), poly(amino acids) and copolymers, terpolymers and combinations thereof. Each possibility represents a separate embodiment of the present invention.

In some currently preferred embodiments, the biodegradable polymer is selected from the group consisting of poly(lactic-co-glycolic acid) (PLGA), poly(lactic acid) (PLA), poly(glycolic acid) (PGA), and any combination thereof. Each possibility represents a separate embodiment of the present invention.

Biodegradable polyesters of poly(lactic acid) (PLA), polyglycolide (PGA), and copolymers of lactide and glycolide referred to as poly(lactide-co-glycolide) (PLGA) are the most common polymers used in biodegradable dosage forms. PLA is a hydrophobic molecule and PLGA degrades faster than PLA because of the presence of more hydrophilic glycolide groups. These biocompatible polymers undergo random, nonenzymatic, hydrolytic cleavage of the ester linkages to form lactic acid and glycolic acid, which are normal metabolic compounds in the body. Resorbable sutures, clips and implants are the earliest applications of these polymers.

In one embodiment, the biodegradable polymer is a lactic acid-based polymer, for example polylactide, or poly(D, L-lactide-co-glycolide) i.e., PLGA. The biodegradable polymer can be present in an amount between about 20% to about 50% w/w of the composition, including each value within the specified range. The lactic acid-based polymer has a monomer ratio of lactic acid to glycolic acid in the range of 100:0 to 0:100, for example in the range of 100:0 to 10:90, and has an average molecular weight from about 1,000 to about 200,000 Daltons, including each value within the specified range. However, it is understood that the amount of biodegradable polymer is determined by parameters such as the duration of use and the like. PLGA polymers are commercially available from multiple suppliers, for example Alkermes (Medisorb polymers), Absorbable Polymers International [formerly Birmingham Polymers (a Division of Durect)], Ashland, Purac and Boehringer Ingelheim.

Encompassed by the present invention are biodegradable carriers comprising poly(lactic-co-glycolic acid) (PLGA) containing lactic and glycolic monomers at a molar ratio of from 50:50 to 85:15 and having an inherent viscosity in the range of about 0.1 to about 0.8 dl/g, including each value within the specified ranges. In some embodiments, the molar ratio of lactic to glycolic monomers in the PLGA is 50:50. In other embodiments, the molar ratio of lactic to glycolic monomers in the PLGA is 75:25. In yet other embodiments, the molar ratio of lactic to glycolic monomers in the PLGA is 85:15.

In some embodiments, the inherent viscosity of the PLGA is in the range of about 0.2 to about 0.7 dl/g, including each value within the specified range. In other embodiments, the inherent viscosity of the PLGA is in the range of about 0.3 to about 0.7 dl/g, including each value within the specified range. In other embodiments, the inherent viscosity of the PLGA is in the range of about 0.4 to about 0.6 dl/g, including each value within the specified range. While a single PLGA polymer can be used in the composition of the present invention, it is contemplated that two or more PLGA polymers can be admixed and used in the ISI composition of the invention to afford a combined inherent viscosity in a desired range. Typically, the PLGA having a higher inherent viscosity and the PLGA having a lower inherent viscosity are present in the composition at a ratio of 2:1 to 1:1, including all ratios within this range.

According to some aspects and embodiments, the PLGA is characterized by acid termini, namely, the end groups of the polymer comprise lactic acid and/or glycolic acid. According to other aspects and embodiments, the PLGA is characterized by ester termini, namely, the end groups of the polymer comprise lactic acid ester and/or glycolic acid ester. A combination of a PLGA having acid termini and a PLGA having ester termini is also encompassed by the present invention.

According to some embodiments, the ratio between the Cariprazine or a pharmaceutically acceptable salt thereof and the PLGA carrier is about 1:1 to about 1:100, including each value within the specified range. Thus, in some embodiments, the ratio between the Cariprazine or a pharmaceutically acceptable salt thereof and the PLGA carrier is about 1:1 to about 1:75, including each value within the specified range. In other embodiments, the ratio between the Cariprazine or a pharmaceutically acceptable salt thereof and the PLGA carrier is about 1:1 to about 1:50, including each value within the specified range. In yet other embodiments, the ratio between the Cariprazine or a pharmaceutically acceptable salt thereof and the PLGA carrier is about 1:1 to about 1:40, including each value within the specified range. Preferably, the ratio between the Cariprazine or a pharmaceutically acceptable salt thereof and the PLGA carrier is about 1:5 to about 1:25, including each value within the specified range.

According to some aspects and embodiments, the ISI composition of the present invention comprises a solvent, which is biocompatible (i.e., non-toxic) and water miscible while also affording the dissolution of the PLGA and Cariprazine active ingredient. Upon administration of the solution, exposure to bodily fluids triggers an exchange between the solvent and water present at the injection site such that the solvent diffuses away from the mixture of polymer and drug while water diffuses into the mixture where it hardens the polymer thereby forming a matrix that entraps or encapsulates the drug within. Suitable biocompatible solvents within the scope of the present invention include, but are not limited to, benzyl alcohol, methyl benzoate, ethyl benzoate, n-propylbenzoate, isopropyl benzoate, butyl benzoate, isobutyl benzoate, tert-butyl benzoate, and benzyl benzoate. Each possibility represents a separate embodiment. Currently preferred is the use of benzyl alcohol as the biocompatible solvent.

The compositions of the present invention may further comprise one or more pharmaceutically acceptable excipient(s) selected from, but not limited to, co-surfactants, solvents/co-solvents including organic solvents, water immiscible solvents, water and water miscible solvents and hydrophilic solvents, preservatives, anti-foaming agents, stabilizers such as antioxidants, tonicity modifiers, buffering agents, pH adjusting agents, sustained release agents, oily components, emulsifiers, channel forming agents, osmotic adjustment agents, or any other excipient known in the art. Each possibility represents a separate embodiment.

Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention.

Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention.

Suitable anti-foaming agents include, but are not limited to, silicon emulsions or sorbitan sesquioleate.

When present, examples of suitable stabilizers to prevent or reduce the deterioration of the components in the compositions of the present invention include, but are not limited to, antioxidants such as glycine, □tocopherol or ascorbate, BHA, BHT, and the like or mixtures thereof. Each possibility represents a separate embodiment of the invention. In some embodiments, the compositions lack a stabilizer. In other embodiments, the compositions lack a component which reduces the surface tension of the compositions. In other embodiments, the compositions lack Tween, Span, poloxamers, tocopherol, cremophor, lecithin, polyethylene glycol and/or polyethylene glycol esters.

Examples of the suitable preservatives for the composition according to the invention may be selected from, but not limited to, quaternary ammonium halides, phenylcarbinol, thimerosal, disodium edetate and phenyl ethyl alcohol. Each possibility represents a separate embodiment of the invention.

Examples of suitable tonicity modifiers for the composition according to the invention include, but are not limited to, mannitol, sodium chloride, and glucose. Each possibility represents a separate embodiment of the invention.

When present, examples of suitable buffering agents for the composition according to the invention include, but are not limited to, acetate buffers, borate buffers, tartrate buffers, lactate buffers, citrate buffers, phosphate buffers (e.g., potassium phosphate monobasic), citric acid/phosphate buffers, carbonate/carbonic acid buffers, succinate/succinic acid buffers, and tris(hydroxymethyl)aminomethane/hydrochloric acid buffers and the like. Each possibility represents a separate embodiment of the invention. In some embodiments, the compositions of the invention lack a buffer. In one embodiment, the compositions lack a buffer selected from the group consisting of phosphate, acetic acid, citric acid, succinic acid, adipic acid, tartaric acid, ascorbic acid, and/or malic acid, and salts thereof.

Suitable pH adjusting agents for the composition according to the invention may be selected from, but not limited to, sodium hydroxide, hydrochloric acid, citric acid, acetic acid, fumaric acid, hydrochloric acid, malic acid, nitric acid, phosphoric acid, propionic acid, sulfuric acid, tartaric acid, or combinations thereof. Each possibility represents a separate embodiment of the invention. Exemplary pH adjusting agents include, but are not limited to, benzoic acid, sorbic acid, fumaric acid, adipic acid, citric acid, succinic acid, glutaric acid, malic acid, malonic acid, tartaric acid, acetic acid, glycolic acid, propionic acid, lauric acid, caprylic acid, capric acid, and myristic acid. Each possibility represents a separate embodiment. A currently preferred pH adjusting agent is benzoic acid.

Suitable sustained release agents include, but are not limited to, bile salts such as sodium glycocholate, sodium deoxycholate, sodium taurocholate, sodium fusidate, sodium glycodeoxycholate, and sodium taurodihydrofusidate. Each possibility represents a separate embodiment. A currently preferred bile salt is sodium deoxycholate. Additional sustained release agents within the scope of the present invention include, but are not limited to, triethyl citrate, triacetin, and lecithin. Each possibility represents a separate embodiment. A currently preferred sustained release agent is triethyl citrate which can also be used as a pH adjusting agent.

In some embodiments, the compositions of the invention lack sodium carboxymethyl cellulose, gelatin, polyvinylpyrrolidone, methylcellulose, and/or acacia. In other embodiments, the compositions of the invention lack hydrochloric acid, acetic acid, phosphoric acid, sodium hydroxide, sodium hydrogen phosphate, calcium carbonate, and/or magnesium hydroxide.

The compositions of the present invention can be prepared by any manner known in the art. For example, the composition can be prepared by dissolving a biodegradable polymer, Cariprazine and optional excipients in a biocompatible organic solvent.

According to the principles of the present invention, the composition may also be provided as a kit comprising the biodegradable polymer, Cariprazine, and biocompatible organic solvent in one compartment or several compartments and instructions for use. The composition may also be provided as a pre-filled syringe, ready for use.

Release Profile

According to the principles of the present invention, the long-acting pharmaceutical compositions of the present invention provide superior therapeutic efficacy as compared to the commercially available daily oral dosage forms of Cariprazine, with reduced incidence of side effects and/or with reduced severity of side effects at the systemic level. In some embodiments, the compositions of the present invention provide prolonged release or prolonged action of Cariprazine and/or its metabolites desmethyl Cariprazine (DCAR) and didesmethyl Cariprazine (DDCAR) in a subject as compared to an immediate release oral formulation such as VRAYLAR®.

Within the scope of the present invention is an ISI composition that provides less than about 20% burst release of the Cariprazine as measured using a dissolution apparatus type II in an aqueous medium containing 0.1% sodium lauryl sulfate (SLS). According to the principles of the present invention, reduced bust release (release of the active ingredient immediately following administration) is afforded thereby minimizing or eliminating adverse effects stemming from systemic exposure to high doses of the Cariprazine active ingredient during the 24-48 hours following administration. In some embodiments, the composition provides from about 2% to about 19% burst release of the Cariprazine in an aqueous medium containing 0.1% SLS as measured using a dissolution apparatus type II. Despite the low burst release, the composition provides release of Cariprazine immediately following administration with no lag time. Thus, gradual release of Cariprazine from the composition is afforded in a continuous manner over a prolonged duration of time of at least 4 weeks following a single administration.

In some embodiments, less than 40% of the Cariprazine is released within 1 week as measured in an aqueous medium containing 0.1% SLS using a dissolution apparatus type II. In other embodiments, less than 30% of the Cariprazine is released within 1 week as measured in an aqueous medium containing 0.1% SLS using a dissolution apparatus type II. In yet other embodiments, less than 20% of the Cariprazine is released within 1 week as measured in an aqueous medium containing 0.1% SLS using a dissolution apparatus type II. Typically, the composition releases from about 8% to about 40% of the Cariprazine or pharmaceutically acceptable salt thereof within 1 week as measured in an aqueous medium containing 0.1% SLS using a dissolution apparatus type II.

In some embodiments, less than 55% of the Cariprazine is released within 2 weeks as measured in an aqueous medium containing 0.1% SLS using a dissolution apparatus type II. In other embodiments, less than 45% of the Cariprazine is released within 2 weeks as measured in an aqueous medium containing 0.1% SLS using a dissolution apparatus type II. In yet other embodiments, less than 35% of the Cariprazine is released within 2 weeks as measured in an aqueous medium containing 0.1% SLS using a dissolution apparatus type II. Typically, the composition releases from about 15% to about 53% of the Cariprazine or pharmaceutically acceptable salt thereof within 2 weeks as measured in an aqueous medium containing 0.1% SLS using a dissolution apparatus type II.

In some embodiments, less than 80% of the Cariprazine is released within 3 weeks as measured in an aqueous medium containing 0.1% SLS using a dissolution apparatus type II. In other embodiments, less than 70% of the Cariprazine is released within 3 weeks as measured in an aqueous medium containing 0.1% SLS using a dissolution apparatus type II. In yet other embodiments, less than 60% of the Cariprazine is released within 3 weeks as measured in an aqueous medium containing 0.1% SLS using a dissolution apparatus type II. Typically, the composition releases from about 36% to about 71% of the Cariprazine or pharmaceutically acceptable salt thereof within 3 weeks as measured in an aqueous medium containing 0.1% SLS using a dissolution apparatus type II.

In some embodiments, less than 90% of the Cariprazine is released within 4 weeks as measured in an aqueous medium containing 0.1% SLS using a dissolution apparatus type II. In other embodiments, less than 80% of the Cariprazine is released within 4 weeks as measured in an aqueous medium containing 0.1% SLS using a dissolution apparatus type II. In yet other embodiments, less than 70% of the Cariprazine is released within 4 weeks as measured in an aqueous medium containing 0.1% SLS using a dissolution apparatus type II. Typically, the composition releases from about 45% to about 86% of the Cariprazine or pharmaceutically acceptable salt thereof within 4 weeks as measured in an aqueous medium containing 0.1% SLS using a dissolution apparatus type II.

In some embodiments, more than 50% of the Cariprazine is released within 5 weeks as measured in an aqueous medium containing 0.1% SLS using a dissolution apparatus type II. In other embodiments, more than 60% of the Cariprazine is released within 5 weeks as measured in an aqueous medium containing 0.1% SLS using a dissolution apparatus type II. In yet other embodiments, more than 70% of the Cariprazine is released within 5 weeks as measured in an aqueous medium containing 0.1% SLS using a dissolution apparatus type II. Typically, the composition releases from about 62% to about 92% of the Cariprazine or pharmaceutically acceptable salt thereof within 5 weeks as measured in an aqueous medium containing 0.1% SLS using a dissolution apparatus type II.

According to some embodiments, the composition provides therapeutically effective plasma concentrations of Cariprazine or its metabolites for at least 4 weeks, for example for about 5 weeks, for about 6 weeks, for about 7 weeks, for about 8 weeks or more, following a single administration. Each possibility represents a separate embodiment. According to some embodiments, the composition provides substantially constant Cariprazine plasma concentrations between about 60 hours to about 600 hours after a single administration, including each value within the specified range. The term "substantially constant" as used herein refers to plasma concentrations that are therapeutically effective and that lack sharp fluctuations such as the hills and valleys that often occur when immediate release Cariprazine formulations are administered.

Therapeutic Uses

The depot formulations of the present invention are particularly useful in methods of treating diseases and conditions for which Cariprazine has been shown to be therapeutically effective at treating.

Thus, in some embodiments, the present invention relates to a method of treating schizophrenia, by administering a depot formulation comprising Cariprazine or a salt thereof, to a schizophrenic patient in need thereof.

In other embodiments, the present invention relates to a method of treating MDD (major depressive disorder), by administering a depot formulation comprising Cariprazine or a salt thereof, to a patient having a major depressive disorder in need thereof.

In other embodiments, the present invention relates to a method of treating bipolar disorder, by administering a depot formulation comprising Cariprazine or a salt thereof, to a patient having a bipolar disorder in need thereof.

In other embodiments, the present invention relates to a method of treating manic or mixed episodes associated with bipolar I disorder, by administering a depot formulation comprising Cariprazine or a salt thereof, to a patient having a bipolar I disorder in need thereof.

In other embodiments, the present invention relates to a method of treating depressive episodes associated with bipolar I disorder (bipolar depression), by administering a depot formulation comprising Cariprazine or a salt thereof, to a patient having a bipolar I disorder in need thereof.

In other embodiments, the present invention relates to a long-acting parenteral pharmaceutical composition in depot form comprising Cariprazine or a salt thereof, for use in the treatment of schizophrenia.

In other embodiments, the present invention relates to a long-acting parenteral pharmaceutical composition in depot form comprising Cariprazine or a salt thereof, for use in the treatment of MDD (major depressive disorder).

In other embodiments, the present invention relates to a long-acting parenteral pharmaceutical composition in depot form comprising Cariprazine or a salt thereof, for use in the treatment bipolar disorder.

In other embodiments, the present invention relates to a long-acting parenteral pharmaceutical composition in depot form comprising Cariprazine or a salt thereof, for use in the treatment of manic or mixed episodes associated with bipolar I disorder.

In other embodiments, the present invention relates to a long-acting parenteral pharmaceutical composition in depot form comprising Cariprazine or a salt thereof, for use in the treatment of depressive episodes associated with bipolar I disorder (bipolar depression).

As used herein, the term "schizophrenia" includes a condition generally described as schizophrenia or a condition having symptoms related thereto. Schizophrenia can be considered a disease with a spectrum of manifestations with various threshold levels of a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. Schizophrenia may be diagnosed by a skilled physician based on personal and medical history, interview consultation and physical examinations.

The term "major depressive disorder" or "MDD" refers to major depression characterized by a combination of symptoms that interfere with a person's ability to work, sleep, study, eat, and enjoy once-pleasurable activities. Major depression is disabling and prevents a person from functioning normally. Some people may experience only a single episode within their lifetime, but more often a person may have multiple episodes.

The term "bipolar disorder" or "BP" includes "bipolar type I disorder" and bipolar "type II disorder" and refers to a chronic psychological/mood disorder which can be characterized by significant mood changes including periods of depression and euphoric manic periods. Bipolar I disorder is a form of BP characterized by periods of severe mood episodes from mania to depression. Bipolar II disorder is a milder form of mood elevation, involving milder episodes of hypomania that alternate with periods of severe depression. The term "treatment of bipolar disorder" includes treatment of manic or mixed episodes associated with bipolar I disorder and/or depressive episodes associated with bipolar I disorder (bipolar depression). Bipolar disorder may be diagnosed by a skilled physician based on personal and medical history, interview consultation and physical examinations.

The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

The term "treating" as used herein refers to taking steps to obtain beneficial or desired results, including clinical results. Beneficial or desired clinical results include, but are not limited to, preventing or slowing the progression of the disease or disorder, or alleviation, amelioration, or slowing the progression, of one or more symptoms associated with the disease being treated such as schizophrenia, MDD, or bipolar disorder (in particular, mania and/or depression).

The term "therapeutically effective amount" as used herein is intended to qualify the amount of Cariprazine that will achieve the goal of treating schizophrenia, MDD, or bipolar disorder, e.g., manic or mixed episodes associated with bipolar I disorder and/or depressive episodes associated with bipolar I disorder (bipolar depression).

Encompassed by the present invention is a combination therapy of Cariprazine or a pharmaceutically acceptable salt of Cariprazine with at least one other active agent. Active agents within the scope of the present invention include, but are not limited to, antipsychotics which may be selected from one or more of amisulpride, nemonapride, remoxipride, sultopride, tiapride, cinuperone, melperone, setoperone, iloperidone, ocaperidone, paliperidone, risperidone, lurasidone, perospirone, revospirone, tiospirone, ziprasidone, amperozide, aripiprazole, bifeprunox, brexpiprazole, amoxapine, asenapine, carpipramine, clocapramine, clorotepine, clotiapine, clozapine, flumezapine, fluperlapine, gevotroline, metitepine, mosapramine, olanzapine, quetiapine, tenilapine, zotepine, or pharmaceutically acceptable salts thereof. Each possibility represents a separate embodiment of the present invention.

According to some embodiments, the depot compositions of the present invention can be administered in vivo to a subject in need thereof. In some embodiments, the "subject" to which the depot composition is administered is a mammal, preferably, but not limited to, a human.

As used herein and in the appended claims, the term "about" refers to +10%.

As used herein and in the appended claims, the singular forms "a", "an", and "the" include plural references unless the context clearly dictates otherwise. Thus, for example, reference to "a biocompatible solvent" includes a plurality of such solvents. It should be noted that the term "and" or the term "or" are generally employed in their sense including "and/or" unless the context clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Examples

General Preparation Method of PLGA-based Injectable In-Situ Implant (ISI) Formulations The ISI depot formulations according to certain embodiments of the present invention were prepared using the following general procedure. PLGA as the biodegradable polymer was dissolved in benzyl alcohol by continuous stirring overnight at room temperature. Cariprazine hydrochloride and optional excipients were dissolved separately in benzyl alcohol and added to the PLGA solution. The mixture was then stirred at room temperature until complete homogenization was achieved.

Example 1

Preparation

A Cariprazine depot formulation termed Formulation A was prepared as follows. An acid terminated PLGA 50:50 having a viscosity of 0.15-0.25 dl/g was mixed with an ester terminated PLGA 50:50 having a viscosity of 0.55-0.75 dl/g at a 1:1 ratio and 30% (w/w) concentration (total solvent). The mixture of dry polymers was suspended in benzyl alcohol and continuously stirred at room temperature until a clear solution was obtained. Then, triethyl citrate (2.4% (w/w) of the formulation) was added to the polymer solution. Cariprazine hydrochloride (10% (w/w) of polymer) was dissolved in benzyl alcohol. Following complete dissolution, the Cariprazine solution was added to the polymer solution and stirred until a homogenous mixture was obtained.

Potency Calculation

The potency of the formulation was analyzed using an HPLC and calculated according to following formula:

$$\text{potency} = \frac{\text{mg } CRPR}{\text{gram formulation}} = \left(\frac{A_{sa} \times C_R}{A_R \times C_S}\right) \times P \times 1000$$

where:
CRPR corresponds to Cariprazine;
$A_{sa}$ corresponds to the peak area of the Cariprazine in the Sample Solution;
$A_R$ corresponds to the peak area of Cariprazine in the Standard Solution;
$C_R$ corresponds to the concentration (mg/mL) of Cariprazine in the Standard Solution;
$C_S$ corresponds to the concentration (mg/mL) of Cariprazine in the Sample Solution;
P corresponds to the potency of standard; and multiplying by 1,000 was performed for unit conversion from mg to gr.

In Vitro Release of Cariprazine from the Formulation

Three types of dissolution media were chosen:
1) 0.1% SLS in water with 0.02% sodium azide,
2) 0.1M HEPES buffer (pH=5.2), and
3) 0.1M acetate buffer (pH=5.0).

In order to evaluate the release of the incorporated Cariprazine from the biodegradable PLGA matrix, a standard dissolution method was employed, using a dissolution apparatus type II.

Sampling Process Description:

Samples of 1500 μl were taken from the dissolution vessel and were centrifugated at 10,000 rpm for 5 minutes. 1000 μl of the supernatant were transferred to a 5.0 ml volumetric flask and brought to volume with the diluent (0.1% $H_3PO_4$: MeOH). The quantitative analysis of the samples was performed using an HPLC instrument.

The release of Cariprazine from Formulation A was tested over a period of 1-2 months. The results of the API release study are depicted in Table 1 and FIG. 1. The percentage of API in the formulation was 2.2%.

TABLE 1

|  | API injected (mg) | Release (%) | | | | |
|---|---|---|---|---|---|---|
|  |  | Burst | 1 week | 2 weeks | 3 weeks | 4 weeks | 5 weeks |
| 0.1M HEPES buffer pH = 5.2 | 43.34 | 12 | 18 | 27 | 94 | 104 |  |
| 0.1% SLS solution | 41.58 | 9 | 37 | 53 | 71 | 86 | 92 |
| 0.1M acetate buffer pH = 5.0 | 40.18 | 8 | 14 | 24 | 61 | 99 |  |

Example 2

Preparation

A Cariprazine depot formulation termed Formulation B was prepared using an ester terminated PLGA 75:25 having a viscosity of 0.4-0.6 dl/g, at 30% (w/w) concentration (total solvent). The formulation was prepared by dissolving the polymer in benzyl alcohol by continuous stirring at room temperature. Cariprazine hydrochloride and benzoic acid (3.7 molar equivalent of Cariprazine) were dissolved in benzyl alcohol. After complete dissolution, the Cariprazine solution was added to the polymer solution and stirred until a homogenous mixture was obtained.

In Vitro Release of Cariprazine from the Formulation

Figure 2:
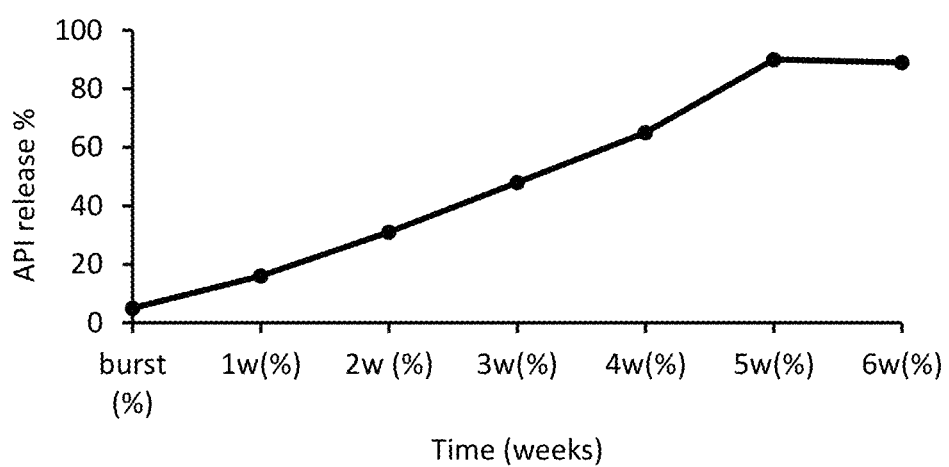
FIG. 2 shows Cariprazine release from Formulation B in 0.1% SLS dissolution medium.

An in-vitro release study was performed as described in Example 1 in an aqueous medium containing 0.1% sodium lauryl sulfate (SLS). The results are depicted in Table 2 and FIG. 2. The percentage of API in the formulation was 2.2%.

TABLE 2

|  | API injected (mg) | Release (%) | | | | | |
|---|---|---|---|---|---|---|---|
|  |  | Burst | 1 week | 2 weeks | 3 weeks | 4 weeks | 5 weeks | 6 weeks |
| 0.1% SLS solution | 42.52 | 5 | 16 | 31 | 48 | 65 | 90 | 89 |

Pharmacokinetic Study

A comparative pharmacokinetic study of Cariprazine following a single dose intramuscular administration of Formulation B (LAI) as compared to repeated doses (oral administrations) of Cariprazine hydrochloride immediate release formulation in male Sprague Dawley rats was performed.

Group allocation and treatment are depicted in Table 3.

TABLE 3

| Group | Treatment (dose) | Animal numbers | Dose volume | Formulation strength (mg/mL) | Route of administration |
|---|---|---|---|---|---|
| 1 | Cariprazine LAI (22 mg/kg) | 1-5 | 1 mL/kg | 22.2 | IM |
| 2 | Cariprazine API (1 mg/kg) | 6-10 | 5 mL/kg | 0.2 mg/ml | PO |

Group 1: Formulation B was administered intramuscularly at the thigh region of rats slowly over 20 seconds on Day 1.
Group 2: Immediate release formulation (0.1% acetic acid in deionized water (d.w.)) was administered orally via gavage once daily up to Day 28.

Figure 3:
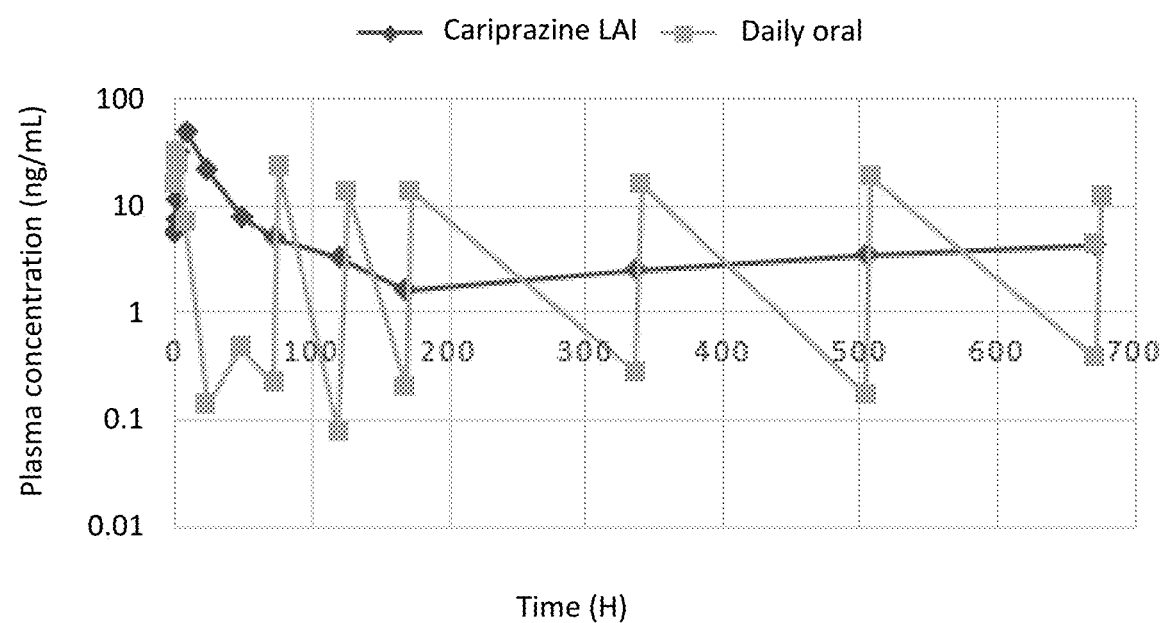
FIG. 3 shows the pharmacokinetic release profile obtained by a single administration of Cariprazine Formulation B vs. the pharmacokinetic release profile obtained by daily oral administrations of an immediate release formulation of Cariprazine in a rat model.

FIG. 3 shows the results of the PK study. While Cariprazine plasma concentrations were comparable, the daily oral administrations resulted in significant fluctuations that were absent when administering the depot formulation according to certain embodiments of the present invention. Accordingly, the formulation of the present invention provides continuous in-vivo release of Cariprazine over at least one month with substantially constant plasma concentrations following a single IM administration.

In Vitro Release of Cariprazine from the Formulation

Figure 4:
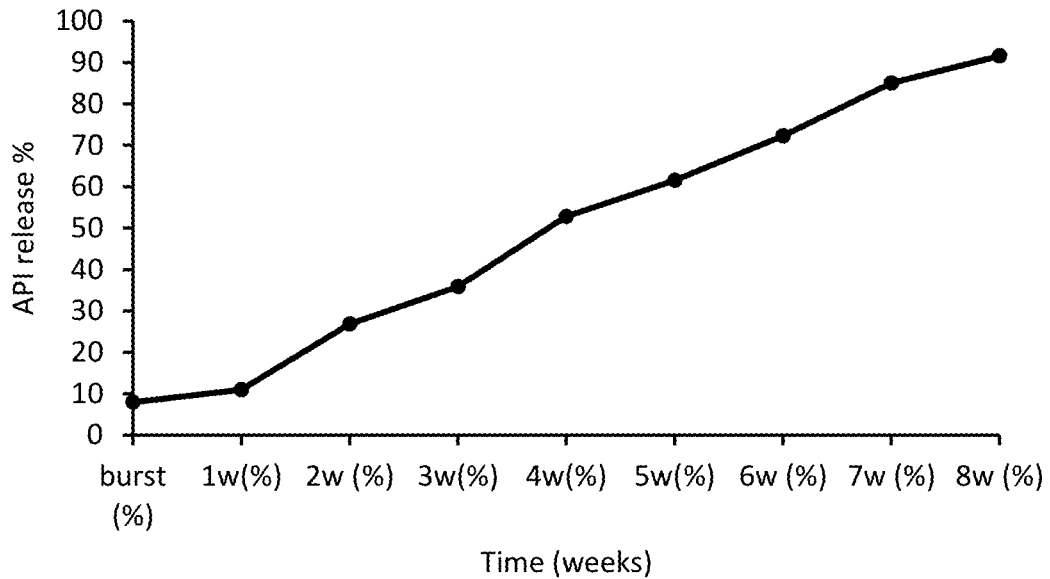
FIG. 4 shows Cariprazine release from Formulation C in 0.1% SLS dissolution medium.

An in vitro release study was performed as described in Example 1 in an aqueous medium containing 0.1% SLS. The results are depicted in Table 4 and FIG. 4. The percentage of API in the formulation was 2.57% and the amount of API injected was 45.03 mg.

TABLE 4

| | Release (%) | | | | | | | | |
|---|---|---|---|---|---|---|---|---|---|
| | Burst | 1 week | 2 weeks | 3 weeks | 4 weeks | 5 weeks | 6 weeks | 7 weeks | 8 weeks |
| 0.1% SLS solution | 8 | 11 | 27 | 36 | 53 | 62 | 72 | 85 | 92 |

Accordingly, Formulation C affords a release extending for two-months.

Example 4

Preparation

A Cariprazine depot formulation termed Formulation D was prepared using an acid terminated PLGA 85:15 having a viscosity of 0.4-0.6 dl/g, at 30% (w/w) concentration (total solvent). The formulation was prepared by dissolving the polymer in benzyl alcohol by continuous stirring at room temperature. Cariprazine hydrochloride was dissolved in benzyl alcohol at 18% concentration ((w/w) of solvent). Following complete dissolution, the Cariprazine solution was added to the polymer solution and stirred until a homogeneous mixture was obtained.

In Vitro Release of Cariprazine from the Formulation

Figure 5:
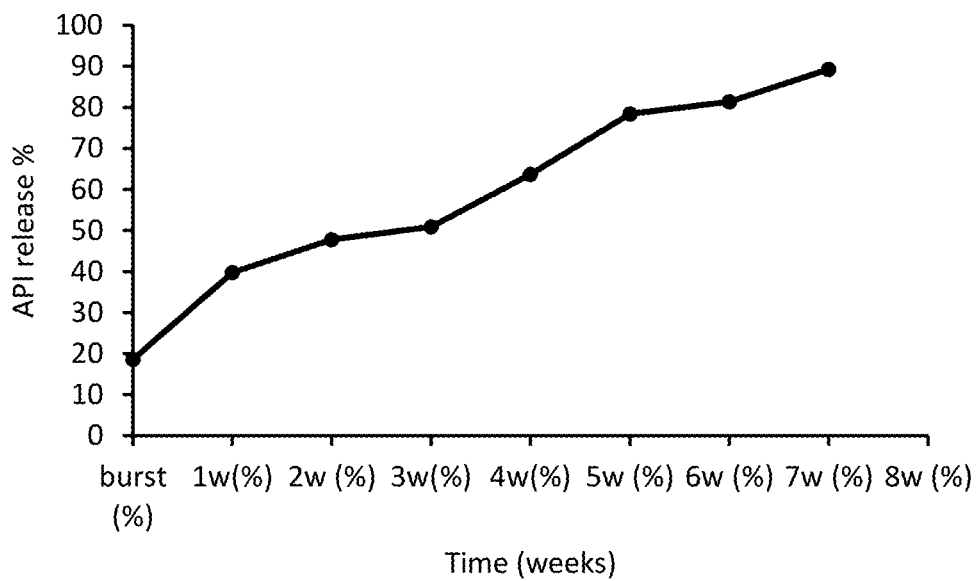
FIG. 5 shows Cariprazine release from Formulation D in 0.1% SLS dissolution medium.

An in vitro release study was performed as described in Example 1 in an aqueous medium containing 0.1% SLS. The results are depicted in Table 5 and FIG. 5. The percentage of API in the formulation was 4.52% and the amount of API injected was 44.32 mg.

TABLE 5

| | Release (%) | | | | | | | | |
|---|---|---|---|---|---|---|---|---|---|
| | Burst | 1 week | 2 weeks | 3 weeks | 4 weeks | 5 weeks | 6 weeks | 7 weeks | 8 weeks |
| 0.1% SLS solution | 19 | 40 | 48 | 51 | 64 | 78 | 81 | 89 | 100 |

Accordingly, Formulation D affords a release extending for two-months.

Example 3

Preparation

A Cariprazine depot formulation termed Formulation C was prepared using an ester terminated PLGA 75:25 having a viscosity of 0.4-0.6 dl/g. The formulation was prepared by dissolving the polymer in benzyl alcohol by continuous stirring at room temperature. Cariprazine hydrochloride was dissolved in benzyl alcohol at 18% concentration ((w/w) of solvent). Following complete dissolution, the Cariprazine solution was added to the polymer solution and stirred until a homogeneous mixture was obtained.

Example 5

Preparation

A Cariprazine depot formulation termed Formulation E was prepared as follows. An acid terminated PLGA 85:15 having a viscosity of 0.4-0.6 dl/g was mixed with an acid terminated PLGA 85:15 having a viscosity of 0.2-0.4 dl/g at a 2:1 ratio and 40% (w/w) concentration. The mixture of polymers was dissolved in benzyl alcohol by continuous stirring at room temperature. Cariprazine hydrochloride (15% (w/w) polymer) was added to the polymer solution and stirred until complete dissolution was achieved and a homogeneous mixture was obtained.

In Vitro Release of Cariprazine from the Formulation

Figure 6:
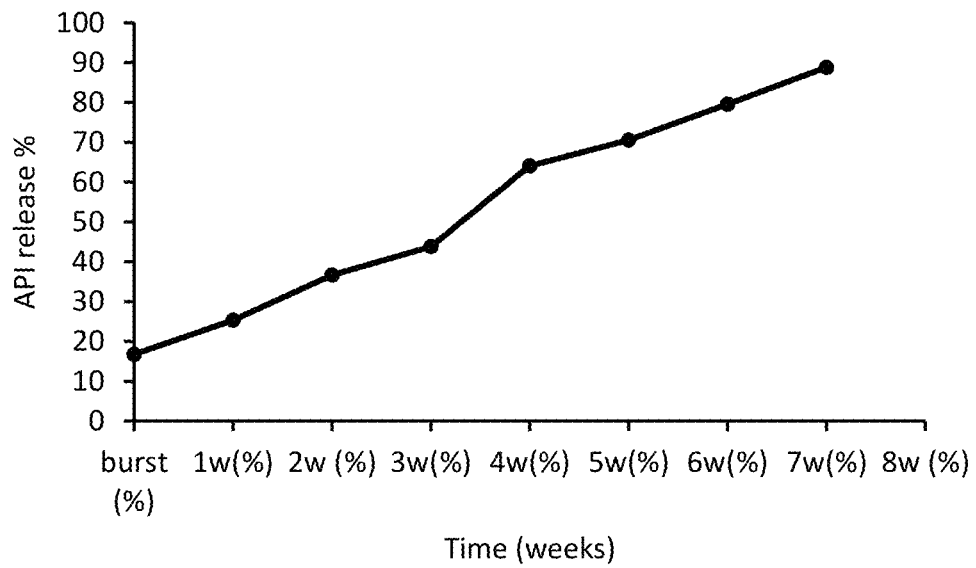
FIG. 6 shows Cariprazine release from Formulation E in 0.1% SLS dissolution medium.

An in vitro release study was performed as described in Example 1 in an aqueous medium containing 0.1% SLS. The results are depicted in Table 6 and FIG. 6. The percentage of API in the formulation was 4.07% and the amount of API injected was 44.4 mg.

TABLE 6

| | Release (%) | | | | | | | |
|---|---|---|---|---|---|---|---|---|
| | Burst | 1 week | 2 weeks | 3 weeks | 4 weeks | 5 weeks | 6 weeks | 7 weeks | 8 weeks |
| 0.1% SLS solution | 17 | 25 | 37 | 44 | 64 | 71 | 80 | 89 | 100 |

Accordingly, Formulation E affords a release extending for two-months.

Example 6

Preparation

A Cariprazine depot formulation termed Formulation F was prepared as follows. An ester terminated PLGA 85:15 having a viscosity of 0.6-0.8 dl/g was mixed with an acid terminated PLGA 85:15 having a viscosity of 0.2-0.4 dl/g at a 1:1 ratio and 30% (w/w) concentration.

The mixture of the polymers was dissolved in benzyl alcohol by continuous stirring at room temperature. Triethyl citrate (2.4% (w/w) of the formulation) was added to the polymer solution. Cariprazine hydrochloride and sodium deoxycholate (0.6 molar equivalents of Cariprazine) were dissolved in benzyl alcohol. Following complete dissolution, the Cariprazine solution was added to the polymer solution and stirred until a homogenous mixture was obtained.

In Vitro Release of Cariprazine from the Formulation

Figure 7:
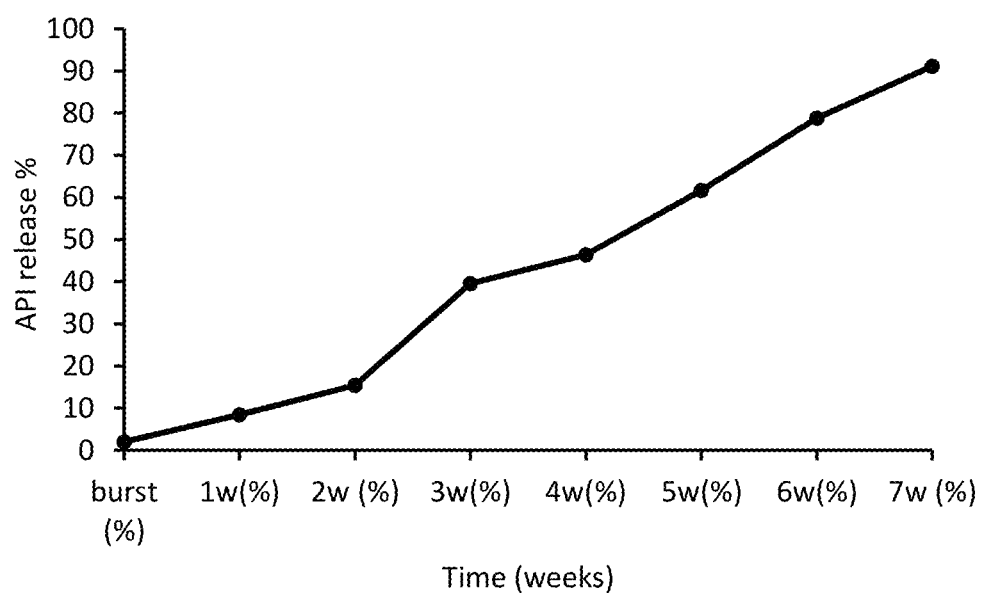
FIG. 7 shows Cariprazine release from Formulation F in 0.1% SLS dissolution medium.

An in vitro release study was performed as described in Example 1 in an aqueous medium containing 0.1% SLS. The results are depicted in Table 7 and FIG. 7. The percentage of API in the formulation was 2.2% and the amount of API injected was 47.09 mg.

TABLE 7

| | Release (%) | | | | | | |
|---|---|---|---|---|---|---|---|
| | Burst | 1 week | 2 weeks | 3 weeks | 4 weeks | 5 weeks | 6 weeks | 7 weeks |
| 0.1% SLS solution | 2 | 8 | 15 | 40 | 45 | 62 | 79 | 91 |

Accordingly, Formulation F affords a release extending for two-months.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A long-acting parenteral pharmaceutical composition in the form of a solution comprising cariprazine or a pharmaceutically acceptable salt thereof, a pharmaceutically acceptable biodegradable carrier comprising poly(lactic-co-glycolic acid) (PLGA), and a biocompatible solvent, wherein the composition is suitable for forming an in situ implant in a subject in need thereof following administration, and wherein the composition releases a therapeutically effective amount of the cariprazine or a pharmaceutically acceptable salt thereof for at least 4 weeks following a single administration.

2. The composition according to claim 1, wherein the pharmaceutically acceptable salt of cariprazine is cariprazine HCl.

3. The composition according to claim 1, which comprises a dose of about 1 to about 100 mg of cariprazine or a pharmaceutically acceptable salt thereof; or which comprises about 1% to about 10% of cariprazine or a pharmaceutically acceptable salt thereof; or which comprises about 20 to about 60 mg/ml of cariprazine or a pharmaceutically acceptable salt thereof.

4. The composition according to claim 1, wherein the pharmaceutically acceptable biodegradable carrier is poly(lactic-co-glycolic acid) (PLGA) comprising lactic acid and glycolic acid end groups; or wherein the carrier is poly(lactic-co-glycolic acid) (PLGA) comprising lactic acid ester and glycolic acid ester end groups.

5. The composition according to claim 1, wherein the poly(lactic-co-glycolic acid) (PLGA) contains a molar ratio of lactic to glycolic monomers of from 50:50 to 85:15.

6. The composition according to claim 1, wherein the poly(lactic-co-glycolic acid) (PLGA) has an inherent viscosity of about 0.1 to about 0.8 dl/g.

7. The composition according to claim 1, which comprises a single PLGA polymer; or which comprises a combination of two or more PLGA polymers having different inherent viscosities.

8. The composition according to claim 1, wherein the biocompatible solvent is selected from the group consisting of benzyl alcohol, methyl benzoate, ethyl benzoate, n-propylbenzoate, isopropyl benzoate, butyl benzoate, isobutyl benzoate, tert-butyl benzoate, and benzyl benzoate.

9. The composition according to claim 8, wherein the biocompatible solvent is benzyl alcohol.

10. The composition according to claim 1, further comprising one or more pharmaceutically acceptable excipients selected from the group consisting of preservatives, sustained release agents, buffering agents, pH adjusting agents, and any combination thereof.

11. The composition according to claim 10, wherein the sustained release agent is a bile salt selected from the group consisting of sodium deoxycholate, sodium glycocholate, sodium taurocholate, sodium fusidate, sodium glycodeoxycholate, and sodium taurodihydrofusidate; or wherein the sustained release agent is selected from the group consisting of triethyl citrate, triacetin, and lecithin.

12. The composition according to claim 10, wherein the pH adjusting agent is a carboxylic acid selected from the group consisting of benzoic acid, sorbic acid, fumaric acid, adipic acid, citric acid, succinic acid, glutaric acid, malic acid, malonic acid, tartaric acid, acetic acid, glycolic acid, propionic acid, lauric acid, caprylic acid, capric acid, and myristic acid.

13. The composition according to claim 1, which provides one or more of the following cariprazine release properties in an aqueous medium containing 0.1% sodium lauryl sulfate as measured using a dissolution apparatus type II:
  (i) less than 20% burst release of the cariprazine or pharmaceutically acceptable salt thereof;
  (ii) less than 40% release of the cariprazine or pharmaceutically acceptable salt thereof within 1 week;
  (iii) less than 55% release of the cariprazine or pharmaceutically acceptable salt thereof within 2 weeks;
  (iv) less than 80% release of the cariprazine or pharmaceutically acceptable salt thereof within 3 weeks;
  (v) less than 90% release of the cariprazine or pharmaceutically acceptable salt thereof within 4 weeks; and
  (vi) more than 50% release of the cariprazine or pharmaceutically acceptable salt thereof within 5 weeks.

14. The composition according to claim 1, which provides one or more of the following cariprazine release properties in an aqueous medium containing 0.1% sodium lauryl sulfate as measured using a dissolution apparatus type II:
  (i) from about 2% to about 19% burst release of the cariprazine or pharmaceutically acceptable salt thereof;
  (ii) from about 8% to about 40% release of the cariprazine or pharmaceutically acceptable salt thereof within 1 week;
  (iii) from about 15% to about 53% release of the cariprazine or pharmaceutically acceptable salt thereof within 2 weeks;
  (iv) from about 36% to about 71% release of the cariprazine or pharmaceutically acceptable salt thereof within 3 weeks;
  (v) from about 45% to about 86% release of the cariprazine or pharmaceutically acceptable salt thereof within 4 weeks; and
  (vi) from about 62% to about 92% release of the cariprazine or pharmaceutically acceptable salt thereof within 5 weeks.

15. The composition according to claim 1, which provides substantially constant cariprazine plasma concentrations between about 60 hours to about 600 hours after a single administration.

16. The composition according to claim 1, which provides prolonged release or prolonged action of cariprazine or its metabolites desmethyl cariprazine (DCAR) and didesmethyl cariprazine (DDCAR) in a subject as compared to an immediate release oral formulation.

17. A method of treating a subject having a disease or disorder selected from schizophrenia, major depressive disorder, and bipolar disorder, the method comprising administering the long-acting parenteral pharmaceutical composition according to claim 1 to the subject.

18. The method according to claim 17, wherein the subject has bipolar disorder comprising manic or mixed episodes associated with bipolar I disorder, or has depressive episodes associated with bipolar I disorder.

19. The method claim 17, comprising administering the long-acting parenteral pharmaceutical composition to the subject at a frequency of about once monthly to about once every 3 months.

20. The method of claim 17, comprising administering the long-acting parenteral pharmaceutical composition to the subject by intramuscular injection.

* * * * *